(12) United States Patent
Duffy

(10) Patent No.: US 12,161,504 B2
(45) Date of Patent: *Dec. 10, 2024

(54) DETECTING FLUID FLOWS USING ULTRASOUND IMAGING SYSTEMS

(71) Applicant: FUJIFILM SONOSITE, INC., Bothell, WA (US)

(72) Inventor: Thomas M. Duffy, Snohomish, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/526,848

(22) Filed: Dec. 1, 2023

(65) Prior Publication Data

US 2024/0108306 A1  Apr. 4, 2024

Related U.S. Application Data

(63) Continuation of application No. 16/805,442, filed on Feb. 28, 2020, now Pat. No. 11,890,132.

(51) Int. Cl.
  *A61B 8/06* (2006.01)
  *A61B 8/00* (2006.01)
  *A61B 8/08* (2006.01)

(52) U.S. Cl.
  CPC .............. *A61B 8/06* (2013.01); *A61B 8/4444* (2013.01); *A61B 8/4488* (2013.01); *A61B 8/463* (2013.01); *A61B 8/488* (2013.01); *A61B 8/5207* (2013.01)

(58) Field of Classification Search
  CPC ....... A61B 8/06; A61B 8/4444; A61B 8/4488; A61B 8/463; A61B 8/488; A61B 8/5207
  See application file for complete search history.

(56) References Cited

U.S. PATENT DOCUMENTS

| 2004/0138563 A1 | 7/2004 | Moehring et al. |
| 2010/0228130 A1 | 9/2010 | Chiang et al. |

(Continued)

FOREIGN PATENT DOCUMENTS

| JP | H0249643 A | 2/1990 |
| JP | 6559762 B2 | 8/2019 |
| WO | 99/08597 A1 | 2/1999 |

OTHER PUBLICATIONS

Supplementary European Search Report and Search Opinion received for European Application No. 21759923.2, mailed on Feb. 28, 2024, 9 pages.

(Continued)

*Primary Examiner* — Colin T. Sakamoto
*Assistant Examiner* — Andrew W Begeman
(74) *Attorney, Agent, or Firm* — Womble Bond Dickinson (US) LLP

(57) ABSTRACT

In one embodiment, a method is provided. The method includes transmitting a first set of ultrasound waves to determine whether there is fluid flow at a target area. The first set of ultrasound waves are transmitted at a first pulse repetition frequency. The method also includes determining whether there is fluid flow in a second area based on the first set of ultrasound waves. The second area is between the target area and an ultrasound probe. The method further includes transmitting a second set of ultrasound waves to detect fluid flow at the target area in response to determining that there is fluid flow in the second area between the target area and the ultrasound probe. The second set of ultrasound waves are directed towards the target area. The second set of ultrasound waves are transmitted at a second pulse repetition frequency.

20 Claims, 9 Drawing Sheets

(56) References Cited

U.S. PATENT DOCUMENTS

| | | |
|---|---|---|
| 2012/0157848 A1 | 6/2012 | Kim |
| 2014/0180032 A1 | 6/2014 | Millett et al. |
| 2014/0257103 A1* | 9/2014 | Jensen ................ G01S 15/8984 |
| | | 600/441 |
| 2015/0151142 A1 | 6/2015 | Tyler et al. |
| 2015/0282787 A1 | 10/2015 | Sato |
| 2015/0313575 A1* | 11/2015 | Tanaka ................ A61B 8/4444 |
| | | 600/447 |
| 2015/0327779 A1 | 11/2015 | Breskin et al. |
| 2016/0220227 A1 | 8/2016 | Kurt et al. |
| 2018/0028161 A1 | 2/2018 | Guenette et al. |
| 2019/0175138 A1 | 6/2019 | Torp et al. |
| 2019/0308038 A1 | 10/2019 | Prus et al. |
| 2021/0121157 A1* | 4/2021 | Wenzel ................ G01S 15/895 |

OTHER PUBLICATIONS

International Preliminary Report on Patentability received for PCT Patent Application No. PCT/US2021/018257, mailed on Aug. 30, 2022, 5 pages.

International Search Report and Written Opinion received for PCT Patent Application No. PCT/US2021/018257, mailed on Jun. 9, 2021, 8 pages.

Office Action received in related Japanese Patent Application No. 2022-551685, mailed Aug. 22, 2024, 6 pages.

* cited by examiner

DETECTING FLUID FLOWS USING ULTRASOUND IMAGING SYSTEMS

This application is a continuation of co-pending U.S. application Ser. No. 16/805,442 filed on Feb. 28, 2020, which is incorporated herein by reference in its entirety.

TECHNICAL FIELD

Aspects of the present disclosure relate to ultrasound imaging systems, and more particularly, to detecting fluid flow using ultrasound imaging systems.

BACKGROUND

Transducers, such as acoustic or ultrasound transducers, are used in medical imaging where an acoustic or ultrasound probe transmits and receives ultrasound waves to create images of the internal tissues of a patient. The ultrasound probe may allow a user (e.g., a doctor, clinician, technician, etc.) to view an image of a target area within the body of the patient. The ultrasound probe may also allow the user to detect the movement of fluid within the body of the patient. For example, the ultrasound probe may allow the user to detect the movement of fluid in a vein, artery, capillary, etc., of a patient.

SUMMARY

In one embodiment, a method is provided. The method includes transmitting a first set of ultrasound waves to determine whether there is fluid flow at a target area. The first set of ultrasound waves are directed towards the target area. The first set of ultrasound waves are transmitted at a first pulse repetition frequency. The method also includes determining whether there is fluid flow in a second area based on the first set of ultrasound waves. The second area is between the target area and an ultrasound probe. The method further includes transmitting a second set of ultrasound waves to detect fluid flow at the target area in response to determining that there is fluid flow in the second area between the target area and the ultrasound probe. The second set of ultrasound waves are directed towards the target area. The second set of ultrasound waves are transmitted at a second pulse repetition frequency.

In one embodiment, an ultrasound probe is provided. The ultrasound probe includes a probe array assembly configured to transmit ultrasound waves. The ultrasound probe also includes a processing device coupled to the probe array assembly. The processing device configured to transmit a first set of ultrasound waves to determine whether there is fluid flow at a target area. The first set of ultrasound waves are directed towards the target area. The first set of ultrasound waves are transmitted at a first pulse repetition frequency. The processing device is further configured to determine whether there is fluid flow in a second area based on the first set of ultrasound waves. The second area is between the target area and the ultrasound probe. In response to determining that there is fluid flow in the second area between the target area and the ultrasound probe, the processing device is further configured to transmit a second set of ultrasound waves to detect fluid flow at the target area. The second set of ultrasound waves are directed towards the target area. The second set of ultrasound waves are transmitted at a second pulse repetition frequency.

In one embodiment, a method is provided. The method includes transmitting a first set of ultrasound waves to determine whether there is fluid flow at a target area. The first set of ultrasound waves are directed towards the target area. The first set of ultrasound waves are transmitted at a first pulse repetition frequency. The method also includes determining whether there is fluid flow in a second area based on the first set of ultrasound waves. The second area is between the target area and an ultrasound probe. The method further includes providing an indication that there is additional fluid flow between the ultrasound probe and the target area in response to determining that there is fluid flow in the second area between the target area and the ultrasound probe.

BRIEF DESCRIPTION OF THE DRAWINGS

The described embodiments and the advantages thereof may best be understood by reference to the following description taken in conjunction with the accompanying drawings. These drawings in no way limit any changes in form and detail that may be made to the described embodiments by one skilled in the art without departing from the spirit and scope of the described embodiments.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

As discussed above, an ultrasound probe may allow a user (e.g., a doctor, clinician, technician, etc.) to view an image of a target area within the body of the patient. The ultrasound probe may also allow the user to detect the movement of fluid within the body of the patient. For example, the ultrasound probe may allow the user to detect the movement of fluid at a target area (e.g., in a vein, artery, capillary, etc.) of a patient. However, if there are one or more other areas where there is fluid movement (e.g., areas between the ultrasound probe and the target area), the ultrasound probe may not be able to accurately detect or determine the fluid movement at the target area.

The implementations, examples, and/or embodiments described herein allow an ultrasound probe and/or an ultrasound imaging system to accurately detect or determine the fluid movement at the target area, even if there is fluid movement in other areas. The ultrasound probe may modify the pulse repetition frequency of ultrasound waves to accurately detect or determine the fluid movement at the target area. The ultrasound probe may also provide an indication (e.g., an error message) if the ultrasound probe is not able to accurately detect or determine the fluid movement at the target area.

Figure 1A:
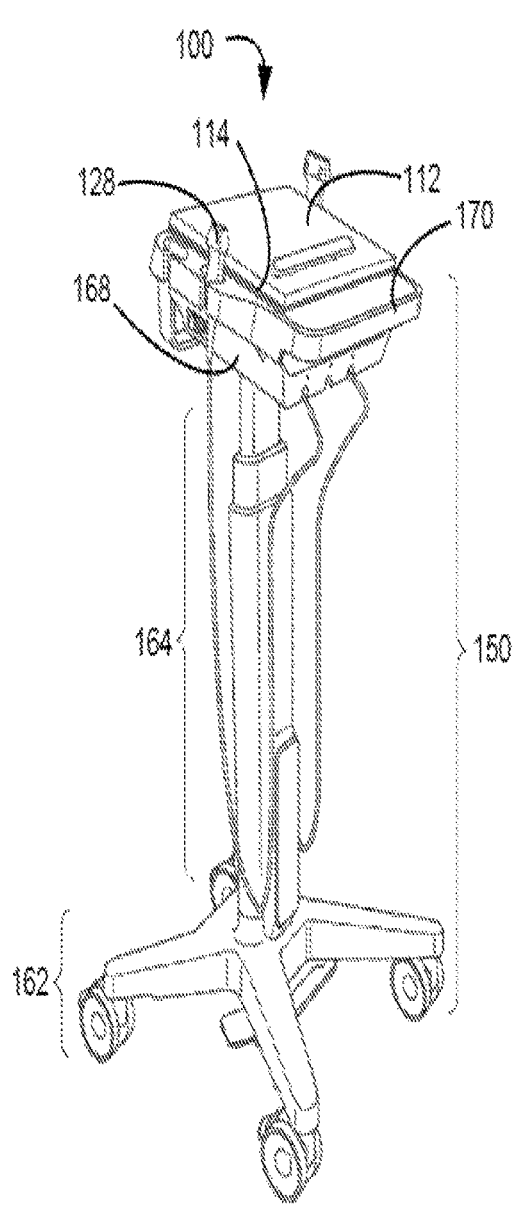
FIG. 1A is an isometric view of an example ultrasound imaging system in accordance with one embodiment of the present disclosure.
Figure 1B:
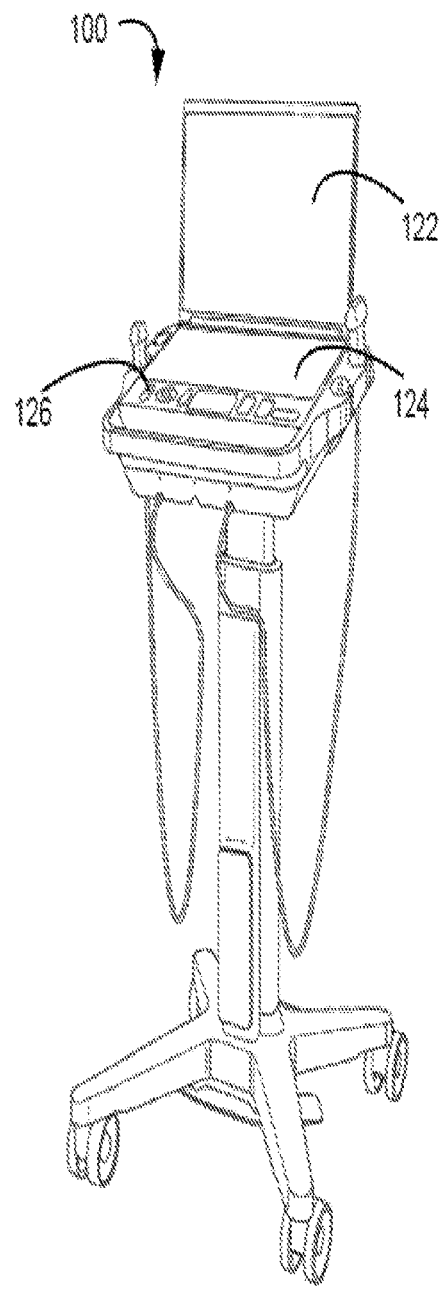
FIG. 1B is an isometric view of an example ultrasound imaging system in accordance with one embodiment of the present disclosure.

FIGS. 1A and 1B show a representative ultrasound imaging system 100 that implements the present technology for detecting fluid movement (e.g., the movement of fluids and/or particles in the fluid) at a target area. In one embodiment, the ultrasound imaging system 100 is a cart-based system that includes an imaging unit removably connected to an adjustable stand. The imaging unit is configured to image human or animal subjects, by sending ultrasound signals or pulses into the target (e.g., the patient's body), receiving reflected echo signals/pulses, and processing the received reflections.

In some embodiments, the imaging unit includes a first interface that is rotatably connected to a second interface, such that a relative angle or orientation between the two interfaces can be changed. For example, in some embodiments, the first and second interfaces are connected through a pin or a hinge joint, such that the first interface and the second interface rotate about an axis corresponding to the joint. In some embodiments, the ultrasound imaging system 100 switches between supported modes according to the relative location, angle, or orientation of the two interfaces. In alternative embodiments, the ultrasound imaging system 100 switches between supported modes according to the relative location, angle, or orientation of one interface with respect to another part of the ultrasound imaging system 100 or a plane defined with respect to the ultrasound imaging system 100, or a part thereof.

In some embodiments, the ultrasound imaging system 100 supports diagnostic imaging modes and one or more procedural modes performed by a medical professional. During a diagnostic examination, the medical professional(s) and/or the operator can use the ultrasound imaging system 100 to passively observe a physiological region of the patient. For example, ultrasound examinations can include one or more of cardiac imaging, abdominal imaging, pelvic imaging, obstetric imaging, Focused Assessment with Sonography in Trauma (FAST) exams, etc.

In comparison, during a procedure, the medical professional(s) and/or the operator uses the ultrasound imaging system 100 to image/track progress while actively performing a medical procedure on a physiological region of the patient to achieve a specific task (e.g., a nerve block). Procedures, in general, can require puncturing of the patient's skin or otherwise inserting a device into the patient's body. Some example examinations and/or procedures can include applications in anesthesiology, angiology, cardiology, emergency medicine, various surgeries, gynecology/obstetrics, otolaryngology, neonatology, ophthalmology, pulmonology, urology, etc. For example, ultrasound-based procedures can include trauma or emergency procedures (e.g., bullet removal or sutures), anesthetic procedures (e.g., perform a nerve block), PICC line procedures, etc.

The ultrasound imaging system 100 is configured to operate in different modes that correspond to the various objectives/scenarios. In some embodiments, the ultrasound imaging system 100 operates in a diagnostics mode and a procedural mode that support one or more diagnostic examinations and one or more procedures, respectively.

In supporting the diagnostic examinations, the ultrasound imaging system 100 operates in a diagnostics mode by target monitoring of the patient's body/tissue. For example, the imaging system processes the received reflections to present a visual depiction of the examined portion of the patient's body. In processing the received reflections, the ultrasound imaging system 100 converts characteristics of the received echo signals (e.g., their amplitude, phase, power, frequency shift, etc.) into data that are quantified and displayed for the user as an image that represents tissue, bone, blood, etc. of the patient's body in the examined region.

In supporting the procedures, the ultrasound imaging system 100 operates in a procedural mode by monitoring the location of medical devices/instruments in relation to the patient's body/tissue. For example, in one embodiment, in the procedural mode, the ultrasound imaging system 100 displays representations of procedural equipment (e.g., needle, stent, catheter/tube, robotic device, etc.) and/or injected material (e.g., contrast, anesthetic, medicine, etc.) relative to an imaged area of the patient's body. Also, in one embodiment, in a procedure mode, the ultrasound imaging system 100 tracks a position, a location, an orientation, etc. of the medical instrument inside a patient's body during the medical procedure.

In some embodiments, a stand for the ultrasound imaging system 100 includes an adjustable hinge configured to facilitate the multiple orientations/positions, and thereby the different operating modes (e.g., diagnostic imaging modes and one or more procedural modes). In at least one embodiment, the adjustable hinge is located in front of a column that supports the imaging unit and/or the docking tray. In one embodiment, the adjustable hinge is further configured to provide different levels of resistance to movement based on a variety of factors, such as a direction of force applied by the operator, a control input from the operator, etc. In one embodiment, the adjustable hinge includes a clutch mechanism configured to provide different levels of resistance according to one or more of a user-operated lever/button, a direction of force or movement, or a combination thereof.

FIG. 1A is an isometric view of a representative ultrasound imaging system 100 in a storage configuration in accordance with an embodiment of the present technology. In some embodiments, the ultrasound imaging system 100 is a conventional clam-shell design with a lid 112 including a display screen (shown closed) and a base portion 114 including processing electronics, power supply, fans, etc. (not shown). The ultrasound imaging system 100 is mounted on a stand 150 with a tilt adjustment as will be explained below. For the storage configuration, the lid 112 can be rotated about a hinge axis and positioned relatively parallel and over the base portion 114. A resulting angle between the two portions can be effectively 0°. In the storage configuration, in one embodiment, the ultrasound imaging system 100 turns off, deactivates, modifies, etc. one or more portions or functionalities thereof, or a combination thereof based on the position and orientation of the imaging system. For example, the ultrasound imaging system 100 turns off or deactivates one or more displays, signal generators, input keys/controllers, software processes, etc.

FIG. 1B is an isometric view of the ultrasound imaging system 100 in a first operating configuration in accordance with an embodiment of the present technology. In some embodiments, the imaging unit includes the lid 112 of FIG. 1A (including e.g., a display screen, a touch screen, etc.) opened with respect to the base portion 114 of FIG. 1A in an operating configuration. The ultrasound imaging system 100 is connected to one or more probes 128 of FIG. 1A that the operator can use to direct ultrasound signals or pulses into the patient's body, and to receive reflected echo signals/pulses. For example, the received reflections are processed to present a visual depiction of the examined portion of the patient's body and/or medical instruments, such as during a diagnostic exam.

In some embodiments, the imaging unit (e.g., the lid 112, the base portion 114, etc.) is attached to the stand 150 of FIG. 1A. The stand 150 includes a column 164 that extends upward from a base 162 (e.g., a wheeled base). The stand 150 further includes a docking tray 168 connected to a top portion of the column 164. The docking tray 168 removably connects to/receives the imaging unit, such as by connecting to and receiving the base portion 114. In some embodiments, the docking tray 168 includes a handle 170 that an operator can grasp to move/displace the ultrasound imaging system 100 and/or orient/position the docking tray 168 and/or the base portion 114.

In some embodiments, an adjustable hinge connects the docking tray 168 to the column 164 and allows the docking tray 168 and a bottom/docked portion of the imaging unit (e.g., the base portion 114 and/or an interface thereon) to rotate relative to a horizontal plane. In one embodiment, the adjustable hinge fixes or holds the docking tray 168 at multiple angles with respect to a horizontal plane. For example, in one embodiment, the adjustable hinge is a barrel-type hinge that includes position stops that limit a range (e.g., between 0-90° below horizontal) of motion/angles for docking tray 168. Other ranges could also be selected based on user/design specifications. For example, in one embodiment, the adjustable hinge includes one or more adjustable motion stops that the user can reposition. Also, in one embodiment, the adjustable hinge includes one or more motion stops that correspond to a specified/designated range of motion. In one embodiment, the hinge has a locking mode (e.g., when a clutch is engaged) that increases the force required to move the hinge so that the imaging system will not change orientation due to gravity, but can easily move to a new orientation if desired. In one embodiment, the hinge includes a button or a lever activated by the weight of the docking tray 168 thereby activating the locking mode. The button or the lever can disengage when the user grabs or lifts the handle 170 or based on the user's manipulation of the clutch mechanism.

To change the operating mode of the imaging system, in one embodiment, the two interfaces are positioned to create an angle in two or more angular ranges. For example, in one embodiment, a medical professional rotates a bottom interface about the horizontal plane to change the operating mode between a diagnostics mode and a procedural mode. To keep the system stable during usage, the column is located behind (i.e., away from the user operating/facing the imaging unit) a center of gravity of the imaging unit and/or the docking tray 168 while adjustable hinge is located below the center of gravity and in front of the column 164. In comparison to having the adjustable hinge co-linear with and directly over the column 164, the above described location of the adjustable hinge increases stability during movement and orientation changes.

In some embodiments, the adjustable hinge includes a clutch mechanism configured to control resistance/friction levels required to move the docking tray 168 and the imaging unit. For example, the clutch mechanism can be configured to provide multiple resistance/friction levels for different directions of movement (e.g., orientation changes of the docking tray 168). The clutch mechanism provides a first resistance level when a user tilts (e.g., rotates about rotational axis of the adjustable hinge) the docking tray 168 upwards, and a second resistance level when the user tilts the docking tray 168 downwards. Also for example, in one embodiment, the clutch mechanism is attached to a control mechanism (e.g., a handle, a lever, a foot pedal, a button, etc.) that is configured to engage and disengage the clutch mechanism according to user manipulation. In one embodiment, the clutch mechanism is configured to provide varying amounts of resistance/friction levels according to the control mechanism, such as force applied thereon or a position thereof. For some embodiments, the clutch mechanism includes a wrap-spring clutch where the tightness of a wound spring can be relieved based on the position of the control mechanism. Further the winding direction provides differing levels of resistance according to different direction (e.g., upward or downward movement at the handle 170) of orientation changes or the direction of the corresponding force. For some embodiments, the clutch mechanism includes a set of plates that are compressed together with differing levels of force according to the control mechanism.

Figure 2:
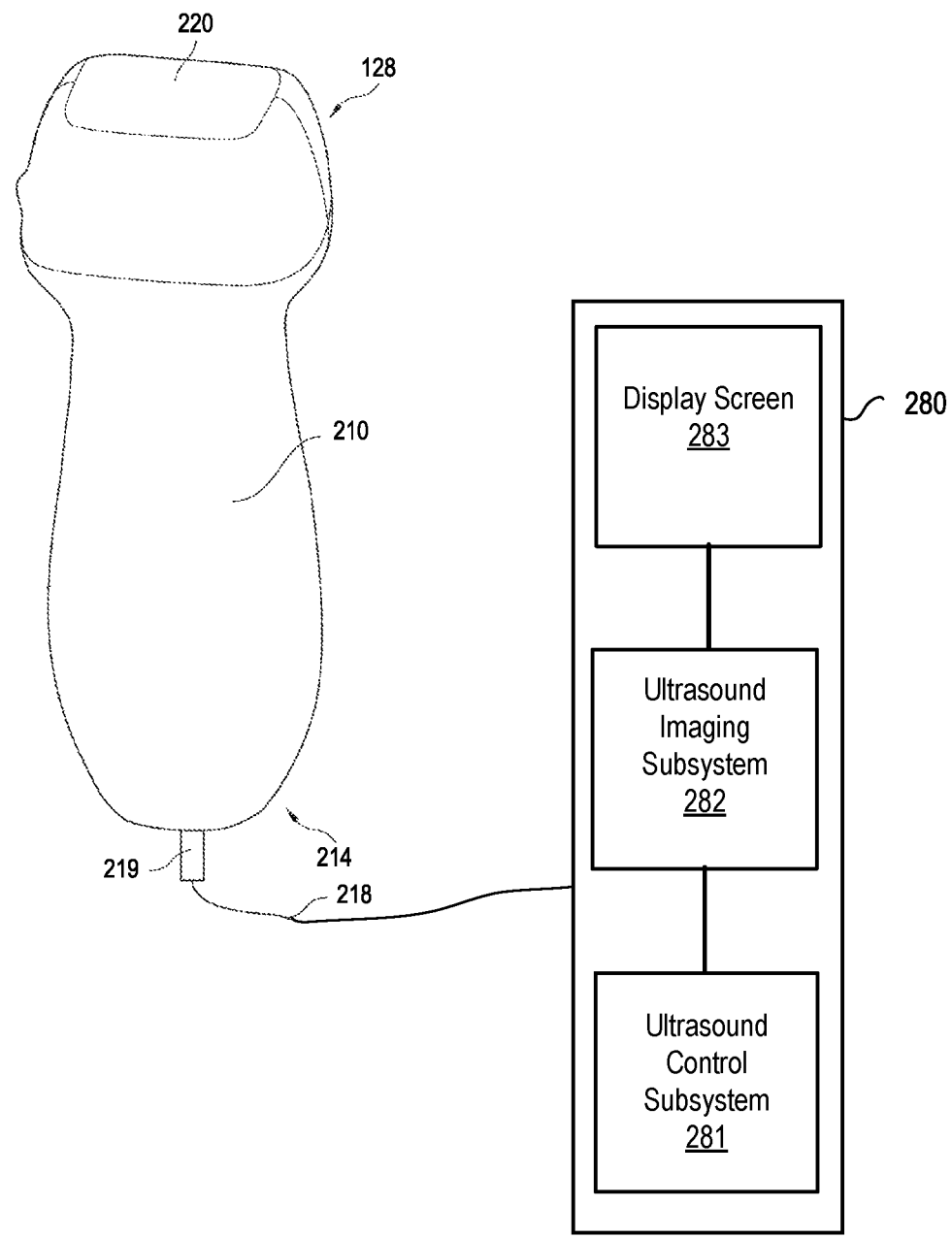
FIG. 2 is a diagram of an example ultrasound imaging system in accordance with one embodiment of the present disclosure.

FIG. 2 illustrates one embodiment of an ultrasound transducer probe having an ultrasound transducer assembly configured in accordance with an embodiment of the disclosed technology. Referring to FIG. 2, ultrasound transducer probe 128 includes an enclosure 210 extending between a distal end portion and a proximal end portion 214. In one embodiment, enclosure 210 of ultrasound transducer probe 128 has a transparent cover that surrounds an inner shell. In one embodiment, the inner shell comprises of metal material (e.g., diecast aluminum, etc.). In one embodiment, the transparent cover comprises transparent plastic (e.g., polysulfone) overmolded on the die cast metal inner shell. In one embodiment, the outer cover and the inner shell create enclosure 210 and work together to transfer heat out of the probe.

Enclosure 210 is configured to carry or house system electronics (e.g., one or more processors, integrated circuits, ASICs, FPGAs, beamformers, batteries and/or other power sources) disposed in an interior portion or cavity of enclosure 210. The system electronics (not shown) are electrically coupled to an ultrasound imaging system 280 via a cable 218 that is attached to the proximal end of the probe by a strain relief element 219.

At the probe tip, a transducer assembly 220 having one or more transducer elements is electrically coupled to the system electronics. In operation, transducer assembly 220 transmits ultrasound energy from the one or more transducer elements toward a subject and receives ultrasound echoes from the subject. The ultrasound echoes are converted into electrical signals by transmit receive circuitry and electrically transmitted to the system electronics and to electronics (e.g., one or more processors, memory modules, beamformers, FPGAs, etc.) in ultrasound imaging system 280 configured to process the electrical signals and form one or more ultrasound images.

Capturing ultrasound data from a subject using an exemplary transducer assembly (e.g., the transducer assembly 220) generally includes generating ultrasound, transmitting ultrasound into the subject, and receiving ultrasound reflected by the subject. A wide range of frequencies of ultrasound may be used to capture ultrasound data, such as, for example, low frequency ultrasound (e.g., less than 15 MHz) and/or high frequency ultrasound (e.g., greater than or equal to 15 MHz) can be used. Those of ordinary skill in the art can readily determine which frequency range to use based on factors such as, for example, but not limited to, depth of imaging and/or desired resolution.

In one embodiment, ultrasound imaging system 280 includes ultrasound control subsystem 281 having one or more processors. At least one processor causes electrical currents to be sent to the transducer(s) of probe 128 to emit sound waves and also receives the electrical pulses from the probe that were created from the returning echoes. A processor processes the raw data associated with the received electrical pulses and forms an image that is sent to ultrasound imaging subsystem 282, which displays the image on display screen 283. Thus, display screen 283 displays ultrasound images from the ultrasound data processed by the processor of ultrasound control subsystem 281.

In one embodiment, the ultrasound system also has one or more user input devices (e.g., a keyboard, a cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data (as illustrated in FIGS. 1A and 1B). These also have not been shown in FIG. 2 to avoid obscuring the techniques disclosed herein.

In one embodiment, the ultrasound probe 128 may be a pulsed wave Doppler ultrasound probe. A pulsed wave Doppler ultrasound probe may be an ultrasound probe that is capable of detecting fluid movement within a target area 325 (e.g., at a gate, a sample volume, a sample, area, etc.). For example, a pulsed wave Doppler ultrasound probe may be able to detect the movement of fluid, such as blood, and/or material within the fluid, at a target area underneath the skin (e.g., underneath or within body tissue) of a patient. A pulsed wave Doppler ultrasound probe may use the Doppler effect to detect the movement of fluid at the target area. For example, the pulsed wave Doppler ultrasound probe may detect changes or variations in the frequency of ultrasound waves. The changes and/or variations in the frequency of the ultrasound waves may be used to determine whether there is fluid movement (e.g., whether there is a fluid moving) at the target area 325. The pulsed wave Doppler ultrasound probe may be able to detect the direction of the movement of the fluid, the amount of fluid moving through the target area, and/or the direction/angle of the movement of the fluid.

Figure 3:
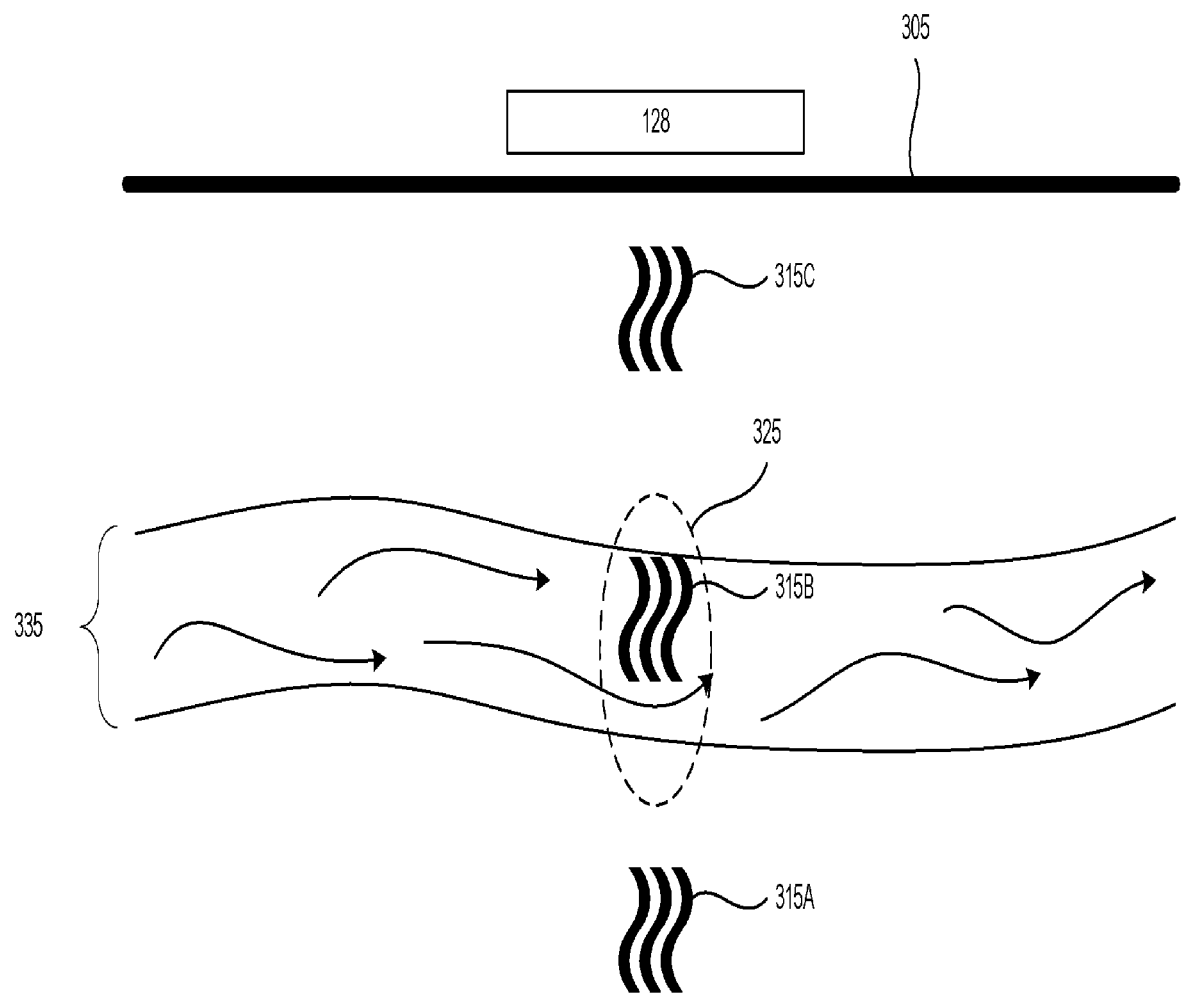
FIG. 3 is a diagram illustrating example ultrasound waves transmitted by an ultrasound probe in accordance with one embodiment of the present disclosure.

FIG. 3 is a diagram illustrating example ultrasound waves 315 transmitted by an ultrasound probe 128 in accordance with one embodiment of the present disclosure. In one embodiment, the ultrasound probe 128 may be able to detect the movement of fluid, such as blood, and/or material within the fluid, at a target area underneath the skin 305 (e.g., underneath or within body tissue) of a patient. The ultrasound probe 128 may detect changes or variations in the frequency of ultrasound waves. The changes and/or variations in the frequency of the ultrasound waves may be used to determine whether there is fluid movement (e.g., whether there is a fluid moving) at the target area 325. The ultrasound probe 128 may be able to detect the direction of the movement of the fluid, the amount of fluid moving through the target area, and/or the direction/angle of the movement of the fluid.

In one embodiment, the ultrasound probe 128 may use pulses of ultrasound waves to determine whether there is fluid movement at the target area 325. For example, as illustrated in FIG. 3, fluid may be moving through a tube 335 underneath the skin 305 of the patient. The tube may be a blood vessel, a capillary, or some other type of structure within the patient's body that allows fluid to flow from one area to another area. The ultrasound probe 128 may transmit ultrasound waves 315 (e.g., pulses of ultrasound waves) downwards beneath the skin 305 of the patient. The ultrasound waves 315 may also be referred to as bursts, pulses, etc., of ultrasound waves. The ultrasound probe 128 may also receive reflections of the ultrasound waves 315. An imaging system (which may be coupled to the ultrasound probe 128, as discussed above) may process the received reflections to generate, provide, present, display, etc., a visual depiction of the target area 325.

Figure 4A:
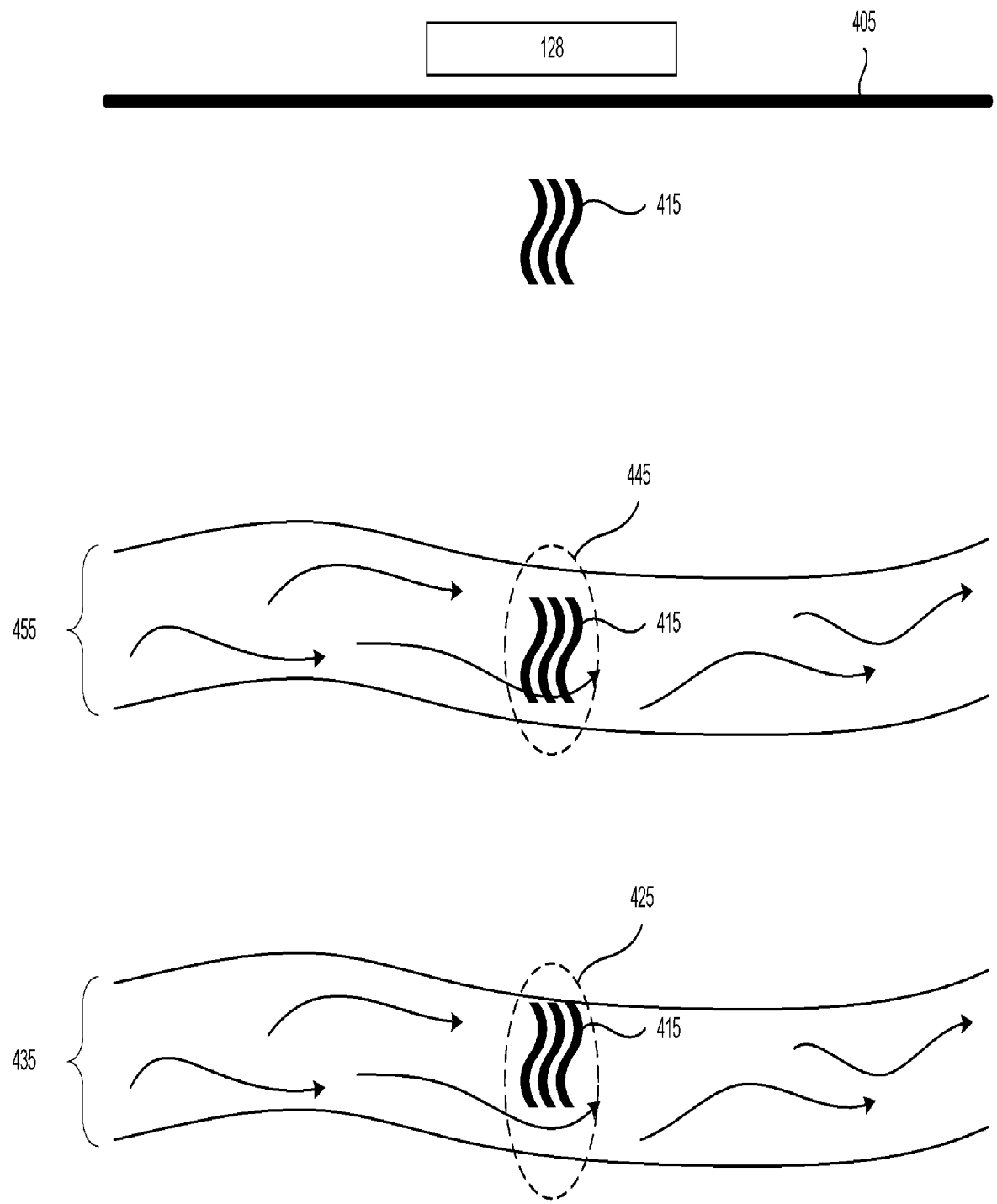
FIG. 4A is a diagram illustrating example ultrasound waves transmitted by an ultrasound probe in accordance with one embodiment of the present disclosure.

FIG. 4A is a diagram illustrating example ultrasound waves 415 transmitted by an ultrasound probe 128 in accordance with one embodiment of the present disclosure. In one embodiment, the ultrasound probe 128 may be a pulsed wave Doppler ultrasound probe. A pulsed wave Doppler ultrasound probe may be an ultrasound probe that is capable of detecting fluid movement within a target area 425 (e.g., at a gate, a sample volume, a sample, area, etc.), as discussed above. For example, the ultrasound probe 128 may use the Doppler effect to detect the movement of fluid at the target area. The ultrasound probe 128 may be able to detect the direction of the movement of the fluid, the amount of fluid moving through the target area 425, and/or the angle of the movement of the fluid. In one embodiment, the ultrasound probe 128 may use pulses of ultrasound waves to determine whether there is fluid movement at the target area 425. For example, as illustrated in FIG. 4, fluid may be moving through a tube 435 (e.g., a blood vessel, capillary, artery, etc.) underneath the skin 405 of the patient. The ultrasound probe 128 may transmit ultrasound waves 415 (e.g., pulses of ultrasound waves) downwards beneath the skin 405 of the patient. The ultrasound probe 128 may also receive reflections of the ultrasound waves 415. An imaging system (which may be coupled to the ultrasound probe 128, as discussed above) may process the reflections (e.g., reflected ultrasound waves) to generate, provide, present, display, etc., a visual depiction of the target area 425 (e.g., one or more images, a video, etc.).

As illustrated in FIG. 4A, fluid may also be moving in a tube 455 is located between the ultrasound probe 128 and the tube 435. Although the ultrasound probe 128 may be able to determine whether there is fluid moving in the target area 425, the ultrasound probe 128 may not be able to accurately determine there is fluid moving in the target area 425 because there is fluid moving in another area 445 above the target area 425. For example, errors and/or aliasing may occur due to the fluid movement in the area 445.

The ultrasound probe 128 may transmit the ultrasound 415 at pulse repetition frequency (PRF). The pulse repetition frequency may be the frequency or period at which the ultrasound probe 128 transmits ultrasound waves towards the target area. For example, the pulse repetition frequency may be 50 hertz (e.g., 50 times a second), a kilohertz (e.g., one thousand times a second) or some other appropriate value. The pulse repetition frequency may also be represented or express in terms of time. For example, the pulse repetition frequency may be every 10 milliseconds, every 200 milliseconds, or some other appropriate time.

As discussed above, the ultrasound probe 128 may transmit the ultrasound waves 415 towards the target area 425 and detect the reflections of the ultrasound waves 415 to determine whether there is movement at the target area 425. If there is fluid movement in an area outside of the target area 425 (e.g., in area 445). This may cause the ultrasound probe be unable to accurately determine whether there is fluid movement at the target area 425 (e.g., may cause errors or aliasing). As illustrated in FIG. 4A, the target area 425 is a first distance below the skin 405. The first distance may be referred to as D1. It may take an amount of time T1 for an ultrasound wave to reach the distance D1 and it may take an equal amount of time T1 for a reflection of the ultrasound wave to reflect back to the ultrasound probe 128. FIG. 4A may illustrate the locations of ultrasound waves at time T1. The total amount of time for an ultrasound wave to be transmitted and reflected back to the ultrasound probe 128 may be 2*T1. As illustrated in FIG. 4A, at time T1, there are ultrasound waves at the target area 425 and the area 445. When the ultrasound probe 128 receives the reflections of the ultrasound waves from the target area 425 at 2*T1, the ultrasound probe may also receive reflections of the ultrasound waves from the area 445. The fluid movement at the area 445 may cause changes/variations in the frequency of the ultrasound waves reflected from the area 445. The fluid movement at the area 445 may also cause changes/variations in the frequency of the ultrasound waves reflected from the target area 425. Because there are two sets of various/ changes to the frequency of the ultrasound waves, the ultrasound probe may not be able to use the variations/ changes in the frequency of the reflected ultrasound waves to accurately detect fluid movement in the target area 425. For example, there may be errors and/or aliasing when the ultrasound probe 128 tries to detect fluid movement in the target are 425.

Figure 4B:
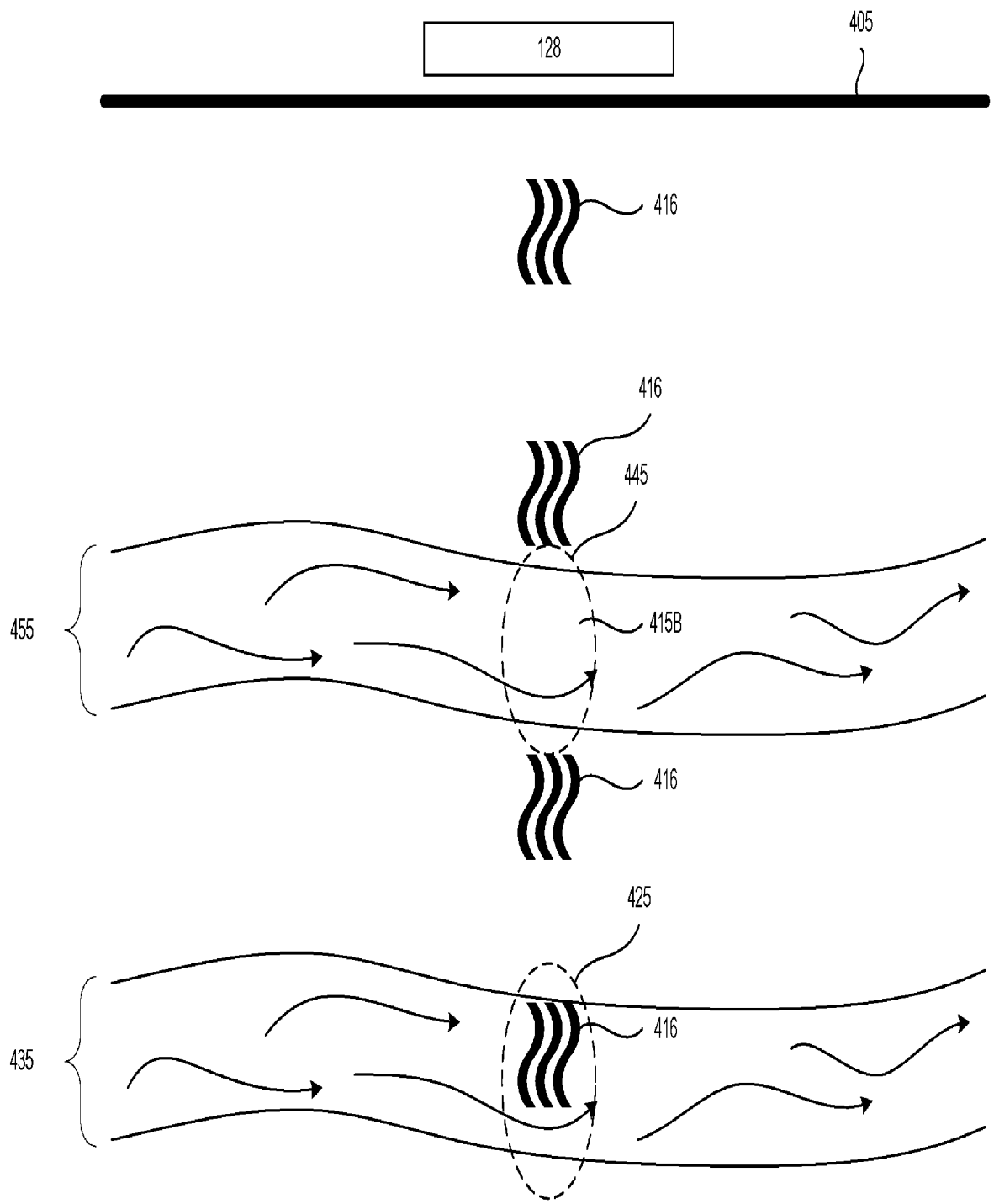
FIG. 4B is a diagram illustrating example ultrasound waves transmitted by an ultrasound probe in accordance with one embodiment of the present disclosure.

FIG. 4B is a diagram illustrating example ultrasound waves 416 transmitted by an ultrasound probe 128 in accordance with one embodiment of the present disclosure. In one embodiment, the ultrasound probe 128 may be a pulsed wave Doppler ultrasound probe. The ultrasound probe 128 may be able to detect the direction of the movement of the fluid, the amount of fluid moving through the target area 425, and/or the direction/angle of the movement of the fluid. In one embodiment, the ultrasound probe 128 may use pulses of ultrasound waves to determine whether there is fluid movement at the target area 425. As illustrated in FIG. 4, fluid may be moving through a tube 435 (e.g., a blood vessel, capillary, artery, etc.) underneath the skin 405 of the patient. The ultrasound probe 128 may transmit ultrasound waves 416 (e.g., pulses of ultrasound waves) downwards beneath the skin 405 of the patient. The ultrasound probe 128 may also receive reflections of the ultrasound waves 416. An imaging system (which may be coupled to the ultrasound probe 128, as discussed above) may process the received reflections to generate, provide, present, display, etc., a visual depiction of the target area 425.

As discussed above, fluid may also be moving in a tube 455 is located between the ultrasound probe 128 and the tube 435. Although the ultrasound probe 128 may be able to determine whether there is fluid moving in the target area 425, the ultrasound probe 128 may not be able to accurately determine there is fluid moving in the target area 425 because there is fluid moving in another area 445 above the target area 425 (as discussed above in conjunction with FIG. 4A). In FIG. 4A, the ultrasound probe 128 transmitted ultrasound waves 415 at a first pulse repetition frequency. As illustrated in FIG. 4B, the ultrasound probe 128 has changed the pulse repetition frequency and is transmitting the ultrasound waves 416 at a second pulse repetition frequency. For example, the ultrasound probe 128 has increased the pulse repetition frequency.

As illustrated in FIG. 4B, the target area 425 is a first distance D1 below the skin 405. It may take an amount of time T1 for an ultrasound wave to reach the distance D1 and it may take an equal amount of time T1 for a reflection of the ultrasound wave to reflect back to the ultrasound probe 128. FIG. 4B may illustrate the locations of ultrasound waves at time T1. The total amount of time for an ultrasound wave to be transmitted and reflected back to the ultrasound probe 128 may be 2*T1. As illustrated in FIG. 4B, at time T1, there are ultrasound waves at the target area 425 and the area 445. When the ultrasound probe 128 receives the reflections of the ultrasound waves 416 from the target area 425 at 2*T1, other ultrasound waves are located at locations/areas which do not have fluid movement. Thus, the reflections of the other ultrasound waves (e.g., the ultrasound waves 416 not located at the target area 425 at time T1) may not change or vary their frequency. This may allow the ultrasound probe 128 to accurately detect fluid movement in the target area 425 based on the variations/changes in the frequency of the ultrasound waves reflected back from the target area 425.

Figure 5:
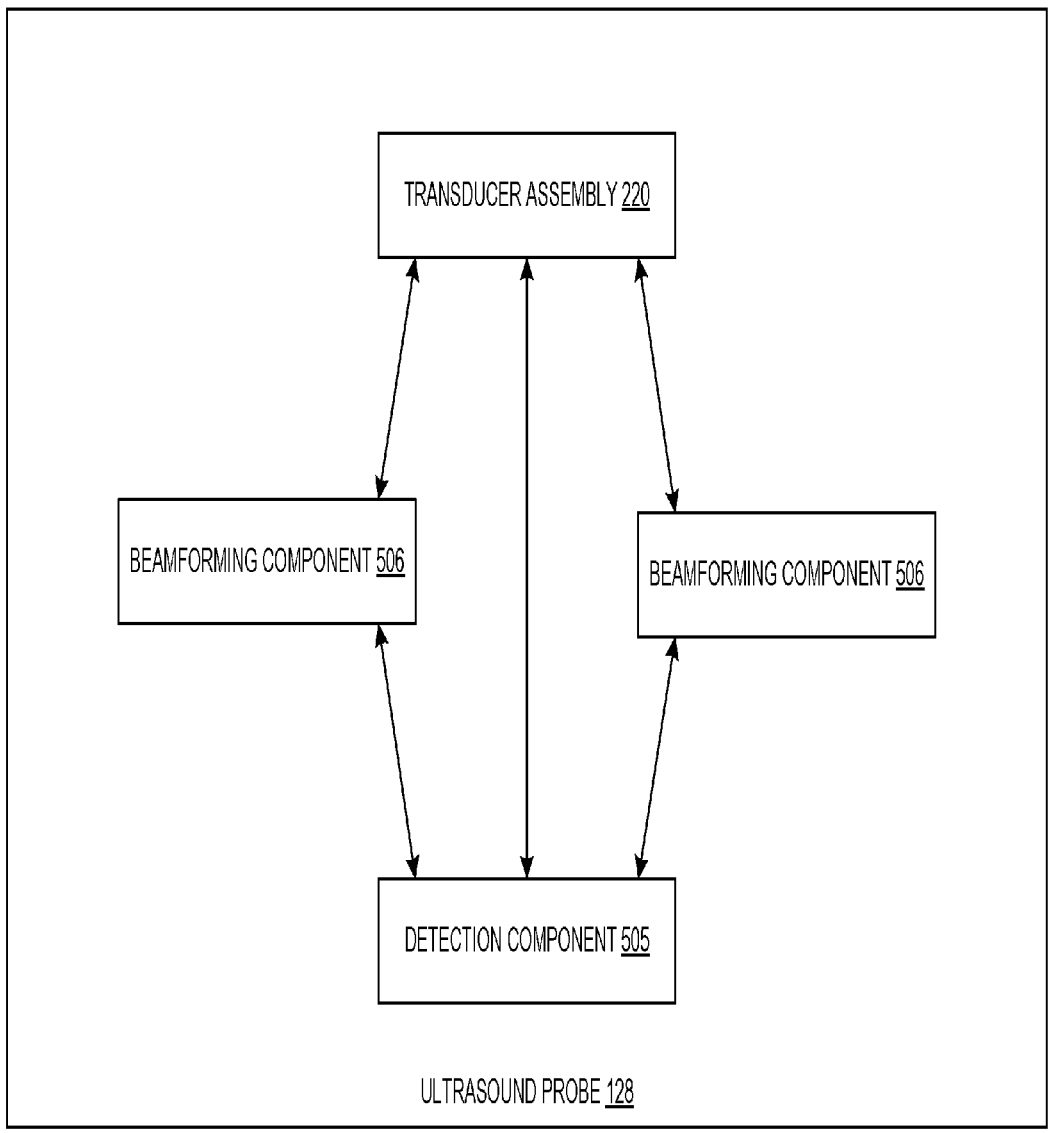
FIG. 5 is a diagram illustrating an example ultrasound probe in accordance with one embodiment of the disclosure.

FIG. 5 is a diagram illustrating an example ultrasound probe 128 in accordance with one embodiment of the disclosure. The ultrasound probe 128 includes a transducer assembly 220, a detection component 505, and beamforming components 506. Each of the detection component 505 and beamforming components 506 may be hardware (e.g., a circuit, a processing device, a processor, a processing core, an FPGA, an ASIC, etc.), software (e.g., an application, a service, etc.), firmware, or a combination thereof.

In one embodiment, the detection component 505 may transmit a first set of ultrasound waves towards a target area to determine whether there is fluid flow (e.g., whether there is fluid moving or flowing) at the target area. The first set of ultrasound waves may be transmitted at a first pulse repetition frequency. For example, as discussed above, the pulses, bursts, etc., of ultrasound waves may be transmitted at fixed periodic time intervals (e.g., every millisecond, every 20 milliseconds, every 100 milliseconds, or some other appropriate period). In one embodiment, the detection component 505 may determine whether there is fluid flow in a second area based on the first set of ultrasound waves (e.g., based on the first set of bursts/pulses of ultrasound waves).

In one embodiment, the detection component 505 may determine whether there is fluid flow in a second area based on the first set of ultrasound waves. As discussed above, reflections of the ultrasound waves may be detected by the ultrasound transducer 128 (e.g., detected using a transducer assembly). The detection component 505 may use the reflections of the ultrasound waves to detect and/or determine whether there is fluid flow at the target area. The second area may be between the target area and the ultrasound probe. As discussed above if there is fluid movement in an area other than the target area, the detection component 505 may not be able to accurately determine the fluid movement at the target area (e.g., due to errors or aliasing).

In one embodiment, the detection component 505 may determine whether there is fluid flow at the target area if the detection component 505 determines that there is no fluid flow at the second area. For example, the detection component 505 may analyze the reflections of the ultrasound waves to determine whether fluid is flowing through a tube (e.g., artery, vein, capillary, etc.) at the target area.

In one embodiment, the detection component 505 may cause one or more images (or a video) of the target to be generated, if the detection component 505 determines that there is fluid flow in the target area. For example, the detection component 505 may transmit ultrasound data (e.g., sensor data, data representing the objects and/or fluid that was detected), to an imaging system which may generate one or more images of the target area. In another example, the detection component 505 may generate the one or more images (e.g., directly generate the one or more images rather than transmitting ultrasound data to another system/component). The one or more images may indicate the movement of the fluid in the target area. For example, the one or more images may include the direction of the fluid flowing in the target area. In another example, the one or more images may indicate the amount of fluid flowing in the target area. In a further example, the one or more images may indicate the angle of the fluid flowing in the target area.

In one embodiment, the detection component 505 may transmit a second set of ultrasound waves (e.g., a second set of bursts/pulses of ultrasound waves) towards the target area to detect fluid flow in the target area if the detection component 505 determine that there is fluid flow in the second area. The second set of ultrasound waves may be transmitted at a second pulse repetition frequency. The second pulse repetition frequency may be different from the first pulse repetition frequency. For example, the second pulse repetition frequency may be higher than the first pulse repetition frequency. In another example, the second pulse repetition frequency may be lower than the first pulse repetition frequency.

In one embodiment, the detection component 505 may determine whether there is fluid flow in a third area based on the second set of ultrasound waves. The third area may be between the target area and the ultrasound probe. The third area may also be different from the second area. For example, the third area may be located at a different location from the second area. In another example, the second area and the third area may not overlap.

In one embodiment, each time the detection component 505 transmits a set of ultrasound waves (at a particular pulse repetition frequencies) and the detection component 505 determines that there is fluid movement in an area outside of the target area, the detection component 505 may determine whether to continuing transmitting ultrasound waves. For example, if fluid movement is detected in the second area or the third area, an area other than the target area, the detection component 505 may determine whether to continue transmitting sets of ultrasound waves, burst/pulses of ultrasound waves, etc.

In one embodiment, an ultrasound imaging system, the ultrasound probe, the detection component 505, etc., may be configured to retransmit ultrasound waves at different pulse repetition frequencies a certain number of time. For example, the ultrasound imaging system, the ultrasound probe, the detection component 505, etc., may be configured to retry transmitting ultrasound waves at different pulse repetition frequencies specified by a user (e.g., a clinician, a doctor, a technician, etc.). The ultrasound imaging system, the ultrasound probe, the detection component 505, etc., may retransmit ultrasound waves (e.g., sets, pulses, bursts, etc., of ultrasound waves) at different pulse repetition frequencies until it reaches a threshold number of retries. In another example, the ultrasound imaging system, the ultrasound probe, the detection component 505, etc., may be configured with a set of pulse repetition frequencies and the ultrasound imaging system, the ultrasound probe, the detection component 505, etc., may retransmit ultrasound waves at each of pulse repetition frequency of the set of pulse repetition frequencies before stopping. In another embodiment, the ultrasound imaging system, the ultrasound probe, the detection component 505, etc., may request input from a user (e.g., user input from a doctor, clinician, technician, etc.) indicating whether the ultrasound imaging system, the ultrasound probe, the detection component 505, etc., should continue retransmitting ultrasound waves at different pulse repetition frequencies. For example, the ultrasound imaging system, the ultrasound probe, the detection component 505, may provide a user interface to allow a user to indicate whether the detection component 505 should continue transmitting ultrasound waves at different pulse repetition frequencies.

In one embodiment, if the detection component 505 determines that the detection component 505 should not continue to transmit sets of ultrasounds waves (e.g., pulses, bursts, etc.,) the detection component 505 may provide an indication that fluid movement was detected in an area other than the target area. For example, the detection component 505 may cause a message (e.g., an error message) to be displayed on a user interface. The message may indicate that fluid movement at a target area may not be accurately detected because there is fluid movement in another area between the ultrasound probe 128 and the target area.

In one embodiment, the detection component 505 may not retransmit ultrasound waves when the detection component 505 determines that there is fluid movement in another area between the ultrasound probe 128 and the target area. The detection component 505 may cause a message (e.g., an error message) to be displayed on a user interface instead. The message may indicate that fluid movement at a target area may not be accurately detected because there is fluid movement in another area between the ultrasound probe 128 and the target area As illustrated in FIG. 5, the ultrasound probe 128 also includes a plurality of beamforming components 506. A beamforming component 506 may perform weighting and summing on the data representing the reflections of the ultrasound signals detected by the transducer assembly 220. The beamforming components may allow to compensate for delays due to the position of transducer elements within the array. In one embodiment, the ultrasound probe 128 includes multiple beamforming components 506 to allow the ultrasound probe 128 to receive and process ultrasound waves or reflections of ultrasound waves at multiple transducer elements simultaneously. For example, a first beamforming component 506 may perform summing and weighting to compensate for different delays in receiving an ultrasound on a transducer element on a right/left side of the transducer assembly 220, and a second beamforming component 506 may perform summing and weighting to compensate for different delays in receiving an ultrasound on a transducer element on in the center of the transducer assembly 220. Because the beamforming components 506 may already exist in the detection component 505 (e.g., the ultrasound probe 128) is able to use the beamforming components 506 when the ultrasound probe 128 is not performing beamforming. For example, when the detection component 505 is detecting fluid movement in a target area, the detection component 505 may be able to use a first set of beamforming components 506 (one or more beamforming components 506) to determine whether there is fluid movement at the target area and may use other sets of beamforming components 506 to determine whether there is fluid movement at other areas, simultaneously.

Figure 6:
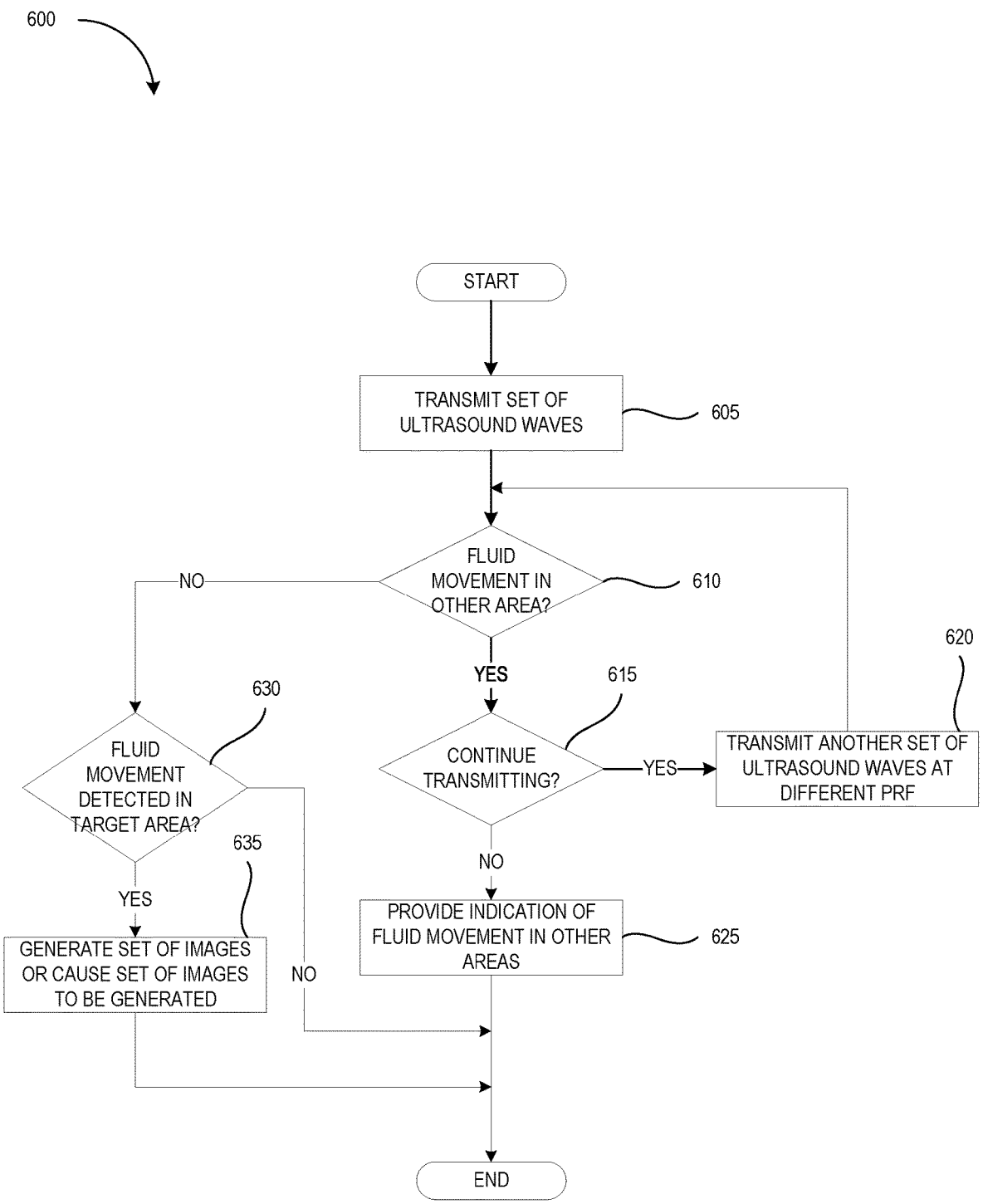
FIG. 6 is a flow diagram of a method of detecting fluid flow in accordance with one embodiment of the present disclosure.

FIG. 6 is a flow diagram of a process 600 of detecting fluid movement in a target area in accordance with one embodiment of the present disclosure. Process 600 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 600 may be performed by one or more of a detection component, an ultrasound probe, an ultrasound imaging system, and/or a computing device.

The process 600 begins at block 605, where the process 600 transmit a set of ultrasound waves at a target area to detect fluid movement at the target area. The ultrasound waves may be transmitted at a first pulse repetition frequency. At block 610, the process 600 may determine whether there is fluid movement in another area that is different than the target area. If there is no fluid movement in other areas, the process 600 may determine whether fluid movement was detected in the target area at block 630. If fluid movement is detected at the target area, the process 600 may generate a set of images or cause a set of images to be generated at block 635. As discussed above, the set of images may indicate the fluid movement at the target area.

If there is fluid movement in areas different or other than the target area, the process 600 may determine whether to continue transmitting ultrasound waves at block 615. For example, the process 600 may determine whether a threshold number of retransmissions have been reached. In another example the process 600 may determine whether a set of different pulse repetition frequencies have been tried. If the process 600 should continue transmitting ultrasound waves, the process may transmit another set of ultrasound waves at a different pulse repetition frequency at block 620. If the process 600 should not continue transmitting ultrasound waves, the process 600 may provide an indication that there is fluid movement in other areas and/or that the process 600 is unable to accurately detect fluid movement at the target area at block 625.

Figure 7:
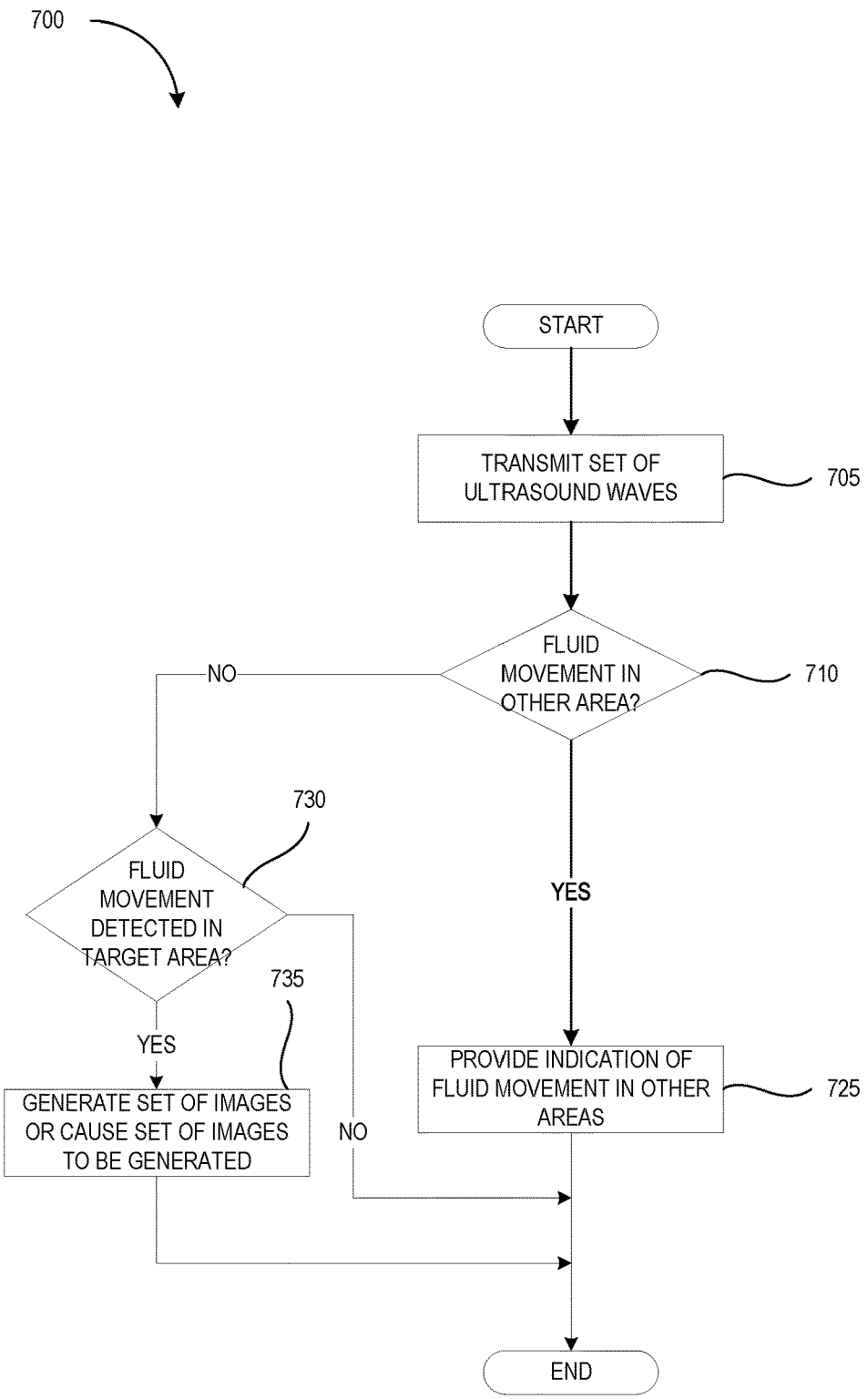
FIG. 7 is a flow diagram of a method of detecting fluid flow in accordance with one embodiment of the present disclosure.

FIG. 7 is a flow diagram of a process 700 of detecting fluid movement in a target area in accordance with one embodiment of the present disclosure. Process 700 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the process 700 may be performed by one or more of a detection component, an ultrasound probe, an ultrasound imaging system, and/or a computing device.

The process 700 begins at block 705, where the process 700 transmit a set of ultrasound waves at a target area to detect fluid movement at the target area. The ultrasound waves may be transmitted at a first pulse repetition frequency. At block 710, the process 700 may determine whether there is fluid movement in another area that is different than the target area. If there is fluid movement in an area that is different than the target area, the process 700 may provide an indication that there is fluid movement in other areas and/or that the process 700 is unable to accurately detect fluid movement at the target area at block 725.

If there is no fluid movement in other areas, the process 700 may determine whether fluid movement was detected in the target area at block 730. If fluid movement is detected at the target area, the process 700 may generate a set of images or cause a set of images to be generated at block 735. As discussed above, the set of images may indicate the fluid movement at the target area.

Figure 8:
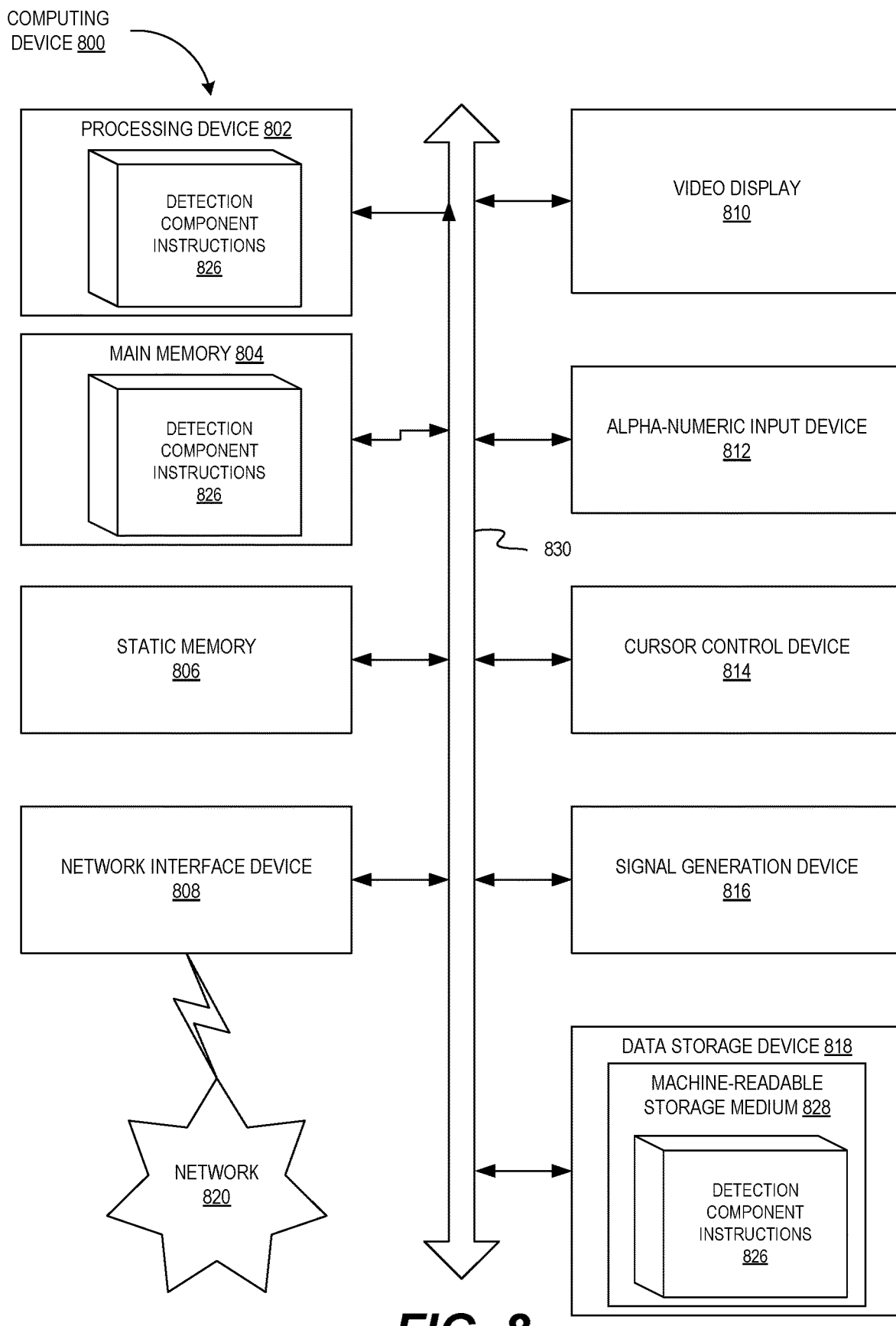
FIG. 8 is a block diagram of an example computing device that may perform one or more of the operations described herein, in accordance with one embodiment of the present disclosure.

FIG. 8 is a block diagram of an example computing device 800 that may perform one or more of the operations described herein, in accordance with some embodiments. Computing device 800 may be connected to other computing devices in a LAN, an intranet, an extranet, and/or the Internet. The computing device may operate in the capacity of a server machine in client-server network environment or in the capacity of a client in a peer-to-peer network environment. The computing device may be provided by a personal computer (PC), a server computing, a desktop computer, a laptop computer, a tablet computer, a smartphone, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein. In some embodiments, the computing device 800 may be one or more of an access point and a packet forwarding component.

The example computing device 800 may include a processing device (e.g., a general purpose processor, a PLD, etc.) 802, a main memory 804 (e.g., synchronous dynamic random access memory (DRAM), read-only memory (ROM)), a static memory 806 (e.g., flash memory and a data storage device 818), which may communicate with each other via a bus 830.

Processing device 802 may be provided by one or more general-purpose processing devices such as a microprocessor, central processing unit, or the like. In an illustrative example, processing device 802 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processing device 802 may also comprise one or more special-purpose processing devices such as an application specific integrated circuit (ASIC), a field programmable gate array (FPGA), a digital signal processor (DSP), network processor, or the like. The processing device 802 may be configured to execute the operations described herein, in accordance with one or more aspects of the present disclosure, for performing the operations and steps discussed herein.

Computing device 800 may further include a network interface device 808 which may communicate with a network 820. The computing device 800 also may include a video display unit 810 (e.g., a liquid crystal display (LCD) or a cathode ray tube (CRT)), an alphanumeric input device 812 (e.g., a keyboard), a cursor control device 814 (e.g., a mouse) and an acoustic signal generation device 816 (e.g., a speaker). In one embodiment, video display unit 810, alphanumeric input device 812, and cursor control device 814 may be combined into a single component or device (e.g., an LCD touch screen).

Data storage device 818 may include a computer-readable storage medium 828 on which may be stored one or more sets of instructions, e.g., instructions for carrying out the operations described herein, in accordance with one or more aspects of the present disclosure. Instructions 826 implementing one or more of a detection component, may also reside, completely or at least partially, within main memory 804 and/or within processing device 802 during execution thereof by computing device 800, main memory 804 and processing device 802 also constituting computer-readable media. The instructions may further be transmitted or received over a network 820 via network interface device 808.

While computer-readable storage medium 828 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

Unless specifically stated otherwise, terms such as "transmitting," "determining," "receiving," "generating," "or the like, refer to actions and processes performed or implemented by computing devices that manipulates and transforms data represented as physical (electronic) quantities within the computing device's registers and memories into other data similarly represented as physical quantities within the computing device memories or registers or other such information storage, transmission or display devices. Also, the terms "first," "second," "third," "fourth," etc., as used herein are meant as labels to distinguish among different elements and may not necessarily have an ordinal meaning according to their numerical designation.

Examples described herein also relate to an apparatus for performing the operations described herein. This apparatus may be specially constructed for the required purposes, or it may comprise a general purpose computing device selectively programmed by a computer program stored in the computing device. Such a computer program may be stored in a computer-readable non-transitory storage medium.

The methods and illustrative examples described herein are not inherently related to any particular computer or other apparatus. Various general purpose systems may be used in accordance with the teachings described herein, or it may prove convenient to construct more specialized apparatus to perform the required method steps. The required structure for a variety of these systems will appear as set forth in the description above.

The above description is intended to be illustrative, and not restrictive. Although the present disclosure has been described with references to specific illustrative examples, it will be recognized that the present disclosure is not limited to the examples described. The scope of the disclosure should be determined with reference to the following claims, along with the full scope of equivalents to which the claims are entitled.

As used herein, the singular forms "a", "an" and "the" are intended to include the plural forms as well, unless the context clearly indicates otherwise. It will be further understood that the terms "comprises", "comprising", "includes", and/or "including", when used herein, specify the presence of stated features, integers, steps, operations, elements, and/or components, but do not preclude the presence or addition of one or more other features, integers, steps, operations, elements, components, and/or groups thereof. Therefore, the terminology used herein is for the purpose of describing particular embodiments only and is not intended to be limiting.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Although the method operations were described in a specific order, it should be understood that other operations may be performed in between described operations, described operations may be adjusted so that they occur at slightly different times or the described operations may be distributed in a system which allows the occurrence of the processing operations at various intervals associated with the processing.

Various units, circuits, or other components may be described or claimed as "configured to" or "configurable to" perform a task or tasks. In such contexts, the phrase "configured to" or "configurable to" is used to connote structure by indicating that the units/circuits/components include structure (e.g., circuitry) that performs the task or tasks during operation. As such, the unit/circuit/component can be said to be configured to perform the task, or configurable to perform the task, even when the specified unit/circuit/component is not currently operational (e.g., is not on). The units/circuits/components used with the "configured to" or "configurable to" language include hardware—for example, circuits, memory storing program instructions executable to implement the operation, etc. Reciting that a unit/circuit/component is "configured to" perform one or more tasks, or is "configurable to" perform one or more tasks, is expressly intended not to invoke 35 U.S.C. 112, sixth paragraph, for that unit/circuit/component. Additionally, "configured to" or "configurable to" can include generic structure (e.g., generic circuitry) that is manipulated by software and/or firmware (e.g., an FPGA or a general-purpose processor executing software) to operate in manner that is capable of performing the task(s) at issue. "Configured to" may also include adapting a manufacturing process (e.g., a semiconductor fabrication facility) to fabricate devices (e.g., integrated circuits) that are adapted to implement or perform one or more tasks. "Configurable to" is expressly intended not to apply to blank media, an unprogrammed processor or unprogrammed generic computer, or an unprogrammed programmable logic device, programmable gate array, or other unprogrammed device, unless accompanied by programmed media that confers the ability to the unprogrammed device to be configured to perform the disclosed function(s).

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:
   transmitting a first set of ultrasound waves, wherein:
      the first set of the ultrasound waves are directed towards a target area; and
      the first set of the ultrasound waves are transmitted at a first pulse repetition frequency;
   determining a fluid flow in a second area based on the first set of the ultrasound waves, wherein the second area is between the target area and an ultrasound probe, wherein the ultrasound probe comprises a plurality of beamforming components comprising a first beamforming component and a second beamforming component, wherein the first beamforming component is to compensate for a first delay in receiving the ultrasound waves on a first transducer element of a transducer assembly and the second beamforming component is to compensate for a second delay in receiving the ultrasound waves on a second transducer element of the transducer assembly, and wherein the first beamforming component is to determine the fluid flow in the target area, and the second beamforming component is to determine the fluid flow in the second area that is separate from the target area, simultaneously, when the ultrasound probe is not performing beamforming.

2. The method of claim 1, wherein determining the fluid flow in the second area is based on a first change of the first pulse repetition frequency of a first set of reflections of the first set of the ultrasound waves from the second area at a first time and a second change of the first pulse repetition frequency of a second set of reflections of the first set of the ultrasound waves from the target area at the first time.

3. The method of claim 1, wherein
   in response to determining that there is no fluid flow in the second area, the first set of the ultrasound waves are used to generate the set of images indicating the fluid flow in the target area on the display device.

4. The method of claim 1, wherein the ultrasound probe comprises a pulsed wave Doppler ultrasound probe.

5. The method of claim 1, further comprising:
   in response to determining the fluid flow in the second area, transmitting a second set of the ultrasound waves to the target area, wherein the second set of the ultrasound waves are transmitted at a second pulse repetition frequency that is different from the first pulse repetition frequency to generate a set of images indicating the fluid flow in the target area on a display device; and
   determining a fluid flow in a third area based on the second set of the ultrasound waves that are transmitted in response to determining that there is the fluid flow in the second area, wherein the third area is between the target area and the ultrasound probe and is separate from the second area.

6. The method of claim 4, further comprising;
   in response to determining that there is the fluid flow in the third area, determining whether to continue transmitting the ultrasound waves, wherein the ultrasound waves are retransmitted at different pulse repetition frequencies until a threshold number of retransmissions is reached; and in response to determining that there is no fluid flow in the third area, using the second set of the ultrasound waves to generate the set of images indicating the fluid flow in the target area on the display device.

7. The method of claim 6, further comprising:
   in response to determining to continue transmitting the ultrasound waves, transmitting a third set of the ultrasound waves to detect the fluid flow at the target area, wherein:
      the third set of the ultrasound waves are directed towards the target area; and
   the third set of the ultrasound waves are transmitted at a third pulse repetition frequency to direct the third set of the ultrasound waves away from the third area and the second area, wherein the third area is located at a different location from the second area; and
   determining a fluid flow in a fourth area based on the third set of the ultrasound waves that are transmitted in response to determining the fluid flow in the third area and determining to continue transmitting the ultrasound waves, wherein the fourth area is between the target area and the ultrasound probe.

8. The method of claim 6, further comprising;
   in response to determining not to continue transmitting the ultrasound waves, providing an indication that there is the fluid flow between the ultrasound probe and the target area.

9. The method of claim 8, wherein the fourth area is separate from the second area and the third area.

10. An ultrasound probe, comprising:
    a probe array assembly configured to transmit ultrasound waves;
    a processing device coupled to the probe array assembly, the processing device configured to:
       transmit a first set of the ultrasound waves, wherein:
          the first set of the ultrasound waves are directed towards a target area; and
          the first set of the ultrasound waves are transmitted at a first pulse repetition frequency;
       determine a fluid flow in a second area based on the first set of the ultrasound waves, wherein the second area is between the target area and the ultrasound probe, wherein the ultrasound probe comprises a plurality of beamforming components comprising a first beamforming component and a second beamforming component, wherein the first beamforming component is to compensate for a first delay in receiving the ultrasound waves on a first transducer element of a transducer assembly and the second beamforming component is to compensate for a second delay in receiving the ultrasound waves on a second transducer element of the transducer assembly, and wherein the first beamforming component is to determine the fluid flow in the target area, and the second beamforming component is to determine the fluid flow in the second area that is separate from the target area, simultaneously, when the ultrasound probe is not performing beamforming.

11. The ultrasound probe of claim 10, wherein determining the fluid flow in the second area is based on a first change of the first pulse repetition frequency of a first set of reflections of the first set of the ultrasound waves from the second area at a first time and a second change of the first pulse repetition frequency of a second set of reflections of the first set of the ultrasound waves from the target area at the first time.

12. The ultrasound probe of claim 10, wherein the processing device is further configured to:
    response to determining that there is no fluid flow in the second area, using the first set of the ultrasound waves to generate the set of images indicating the fluid flow in the target area on the display device.

13. The ultrasound probe of claim 10, wherein the ultrasound probe comprises a pulsed wave Doppler ultrasound probe.

14. The ultrasound probe of claim 10, wherein the processing device is further configured to:
   in response to said determine the fluid flow in the second area, transmit a second set of the ultrasound waves to the target area, wherein the second set of the ultrasound waves are transmitted at a second pulse repetition frequency that is different from the second pulse repetition frequency to generate a set of images indicating the fluid flow in the target area on a display device; and
   determine a fluid flow in a third area based on the second set of the ultrasound waves that are transmitted in response to determining that there is the fluid flow in the second area, wherein the third area is between the target area and the ultrasound probe and is separate from the second area.

15. The ultrasound probe of claim 14, wherein the processing device is further configured to:
   in response to determining that there is the fluid flow in the third area, determine whether to continue transmitting the ultrasound waves, wherein the ultrasound waves are retransmitted at different pulse repetition frequencies until a threshold number of retransmissions is reached; and
   in response to determining that there is no fluid flow in the third area, use the second set of the ultrasound waves to generate the set of images indicating the fluid flow in the target area on the display device.

16. The ultrasound probe of claim 13, wherein the processing device is further configured to:
   in response to determining to continue transmitting the ultrasound waves, transmit a third set of the ultrasound waves to detect the fluid flow at the target area, wherein:
      the third set of the ultrasound waves are directed towards the target area; and
      the third set of the ultrasound waves are transmitted at a third pulse repetition frequency to direct the third set of the ultrasound waves away from the third area and the second area, wherein the third area is located at a different location from the second area; and
      determine a fluid flow in a fourth area based on the third set of the ultrasound waves that are transmitted in response to determining the fluid flow in the third area and determining to continue transmitting the ultrasound waves, wherein the fourth area is between the target area and the ultrasound probe.

17. The ultrasound probe of claim 14, wherein the processing device is further configured to:
   in response to determining not to continue transmitting the ultrasound waves, provide an indication that there is the fluid flow between the ultrasound probe and the target area.

18. The ultrasound probe of claim 17, wherein the fourth area is separate from the second area and the third area.

19. A method, comprising:
   transmitting a first set of ultrasound waves, wherein:
      the first set of the ultrasound waves are directed towards a target area; and
      the first set of the ultrasound waves are transmitted at a first pulse repetition frequency;
   determining a fluid flow in a second area based on the first set of the ultrasound waves, wherein the second area is between the target area and an ultrasound probe;
   providing an indication that there is the fluid flow between the ultrasound probe and the target area, wherein the ultrasound probe comprises a plurality of beamforming components comprising a first beamforming component and a second beamforming component simultaneously, wherein the first beamforming component is to compensate for a first delay in receiving the ultrasound waves on a first transducer element of a transducer assembly and the second beamforming component is to compensate for a second delay in receiving the ultrasound waves on a second transducer element of the transducer assembly, and wherein the first beamforming component is to determine the fluid flow in the target area, and the second beamforming component is to determine the fluid flow in the second area that is separate from the target area, simultaneously, when the ultrasound probe is not performing beamforming.

20. The method of claim 19, further comprising:
   in response to determining the fluid flow in the second area, transmitting a second set of the ultrasound waves to the target area, wherein the second set of the ultrasound waves are transmitted at a second pulse repetition frequency that is different from the first pulse repetition frequency to generate a set of images indicating the fluid flow in the target area on a display device;
   and
   determining a fluid flow in a third area based on the second set of the ultrasound waves that are transmitted in response to determining that there is the fluid flow in the second area, wherein the third area is between the target area and the ultrasound probe and is separate from the second area, wherein determining the fluid flow in the second area is based on a first change of the first pulse repetition frequency of a first set of reflections of the first set of the ultrasound waves from the second area at a first time and a second change of the first pulse repetition frequency of a second set of reflections of the first set of the ultrasound waves from the target area at the first time.

* * * * *